(12) United States Patent
Stopek

(10) Patent No.: US 9,034,357 B2
(45) Date of Patent: May 19, 2015

(54) ANTI-ADHESION BARRIER

(75) Inventor: Joshua B. Stopek, Yalesville, CT (US)

(73) Assignee: Covidien LP, Mansfield, MA (US)

( * ) Notice: Subject to any disclaimer, the term of this patent is extended or adjusted under 35 U.S.C. 154(b) by 2589 days.

(21) Appl. No.: 11/660,577

(22) PCT Filed: Aug. 16, 2005

(86) PCT No.: PCT/US2005/028985
§ 371 (c)(1),
(2), (4) Date: Feb. 16, 2007

(87) PCT Pub. No.: WO2006/023444
PCT Pub. Date: Mar. 2, 2006

(65) Prior Publication Data
US 2007/0280990 A1    Dec. 6, 2007

Related U.S. Application Data

(60) Provisional application No. 60/602,225, filed on Aug. 17, 2004.

(51) Int. Cl.
*A61L 27/48* (2006.01)
*A61L 31/12* (2006.01)
*A61F 13/00* (2006.01)
(Continued)

(52) U.S. Cl.
CPC ............ *A61L 27/48* (2013.01); *A61B 17/0401* (2013.01); *A61B 17/06166* (2013.01); *A61B 17/064* (2013.01); *A61F 13/00008* (2013.01); *A61F 13/00063* (2013.01); *A61F 13/00987* (2013.01); *A61F 2013/00157* (2013.01); *A61F 2013/00221* (2013.01); *A61F 2013/00225* (2013.01); *A61F 2013/00229* (2013.01); *A61F 2013/00357* (2013.01); *A61F 2013/00404* (2013.01); *A61F 2013/00451* (2013.01); *A61F 2013/00519* (2013.01); *A61F 2013/0091* (2013.01); *A61F 2013/00927* (2013.01); *A61L 31/129* (2013.01)

(58) Field of Classification Search
CPC . A61L 27/48; A61L 31/129; A61F 13/00008; A61F 13/00063; A61F 13/00987; C08L 33/10
USPC .......... 424/423, 141.11; 604/892.1; 623/1.13; 514/772.7; 428/308.4
See application file for complete search history.

(56) References Cited

U.S. PATENT DOCUMENTS 4,954,593 A    9/1990  Vara et al.
5,226,902 A *  7/1993  Bae et al. ................... 604/892.1
(Continued)

FOREIGN PATENT DOCUMENTS

EP    0 496 813    12/1994
EP    1 498 420    1/2005
(Continued)

OTHER PUBLICATIONS

Iwasaki et al., "In vitro and ex vivo blood compatibility study of 2-methacryloyloxyethyl phosphorylcholine (MPC) copolymer-coated hemodialysis hollow fibers", *Journal of Artificial Organs* (2003), 6(4):260-266.
(Continued)

*Primary Examiner* — Blessing M Fubara

(57) ABSTRACT

The present disclosure relates to medical devices comprising at least a first film layer and at least a second gel layer and to methods for preparing such devices.

13 Claims, 2 Drawing Sheets

(51) Int. Cl.
*C08L 33/10* (2006.01)
*A61B 17/04* (2006.01)
*A61B 17/06* (2006.01)
*A61B 17/064* (2006.01)

(56) References Cited

U.S. PATENT DOCUMENTS

| | | | |
|---|---|---|---|
| 5,914,182 | A * | 6/1999 | Drumheller ............... 428/308.4 |
| 6,403,655 | B1 * | 6/2002 | Bezwada et al. ........... 514/772.7 |
| 2002/0165205 | A1 | 11/2002 | Kubo et al. |
| 2002/0187182 | A1 | 12/2002 | Kramer et al. |
| 2003/0104068 | A1 * | 6/2003 | Mathiowitz et al. .......... 424/491 |
| 2003/0157193 | A1 | 8/2003 | McDonald et al. |
| 2004/0018228 | A1 | 1/2004 | Fischell et al. |
| 2005/0208093 | A1 | 9/2005 | Glauser et al. |
| 2006/0129225 | A1 * | 6/2006 | Kopia et al. ................. 623/1.13 |
| 2006/0193884 | A1 | 8/2006 | Stopek et al. |
| 2007/0032666 | A1 | 2/2007 | Read et al. |
| 2008/0033106 | A1 | 2/2008 | Koroskenyi et al. |

FOREIGN PATENT DOCUMENTS

| | | | |
|---|---|---|---|
| WO | WO 93/21858 | * | 11/1993 |
| WO | WO93/21858 | A | 11/1993 |
| WO | WO97/35533 | A | 10/1997 |
| WO | WO 2007/133782 | A1 | 11/2007 |

OTHER PUBLICATIONS

Nakabayashi et al., "Copolymers of 2-methacryloyloxyethyl phosphorylcholine (MPC) as biomaterials", *Bio-Medical Materials and Engineering* (2004), vol. 14, 345-354.

Search Report from International Application No. PCT/US08/63147 dated Aug. 4, 2008.

Search Report from International Application No. PCT/US08/63149 dated Aug. 11, 2008.

Iwasaki Y; et al. "Reduced Adhesion of Blood Cells to Biodegradable Polymers by Introducing Phosphorylcholine Moieties" *Journal of Biomedical Materials Research Part A,* vol. 65a, 2003, pp. 164-169, XP002502022.

Meng S; et al. "Phosphorylcholine end-capped poly-[epsilon]-caprolactone: A Novel Biodegradable Material With Improved Antiadsorption Property" *Journal of Applied Polymer Science,* vol. 103, Jan. 15, 2007, pp. 989-997, XP002502023.

Watanabe J; et al. "Change in cell adhesion property on cytocompatible interface using phospholipid polymer grafted with poly(D,L-lactic acid) segment for tissue engineering" *Science and Technology of Advanced Materials,* vol. 4, 2003, pp. 539-544, XP002502024.

Watanabe J. et al. "Cell Engineering Biointerface Focusing on Cytocompatibility Using Phospholipid Polymer With an Isomeric Oligo(Lactic Acid) Segment" *Biomacromolecules,* vol. 6, Apr. 2, 2005, pp. 1797-1802, XP002502025.

Watanabe et al. "Cytocompatible Biointerface on Poly(Lactic Acid) by Enrichment With Phosphorylcholine Groups for Cell Engineering" *Materials Science and Engineering C,* vol. 27, No. 2, Feb. 7, 2007, pp. 227-231, XP005877903 ISSN: 0928-4931.

Kristensen E M E; et al. "Photoelectron Spectroscopy Studies of the Functionalization of a Silicon Surface With a Phosphorylcholine-Terminated Polymer Grafted Onto (3-Aminopropyl)Trimethoxysilane" *Langmuir,* vol. 22, Oct. 12, 2006, pp. 9651-9657, XP002502026.

Zalipsky S et al.: "Long Circulating, Cationic Liposomes Containing Amino-Peg-Phosphatidylethanolamine" *FEBS Letters,* vol. 353, No. 1, Oct. 10, 1994, pp. 71-74, XP000858869 ISSN: 0014-5793.

European Search Report for EP 08 252691.4-2102 mailed Nov. 13, 2008 (10 pages).

European Search Report for EP 05786516.4-2124 date of completion is Jul. 14, 2009 (4 pages).

WO2006/023444Search report date of Mailing Feb. 21, 2006.

* cited by examiner

ANTI-ADHESION BARRIER

CROSS REFERENCE TO RELATED APPLICATIONS

This application claims priority from PCT/US2005/028985 filed Aug. 16, 2005 which claims priority to U.S. Provisional Application Ser. No. 60/602,225 filed Aug. 17, 2004 the disclosures of which are incorporated herein in their entirety by this reference.

BACKGROUND

1. Technical Field

This disclosure relates to multi-layer devices for preventing tissue adhesion and promoting tissue growth.

2. Background of Related Art

In the field of internal medical care, such as internal surgery, there is a need for tissue regeneration devices which may prevent complications such as adhesions in the post-operative healing period. Adhesions which may be formed include the adhesion of tissue to tissue or of tissue to bone. It has been known to separate adjacent internal bodily surfaces by interposing a mesh or film so that during tissue regeneration following surgery no contact exists between the surfaces. One material which has been employed to prevent adhesions is an expanded polytetrafluoroethylene material known as Gore-Tex®. This material, however, is not hemostatic and is non-degradable by the human body. Thus the implant remains in the body, and, if necessary, must be removed surgically following the healing process. Another material is a mesh barrier of carboxymethylcellulose known as Interceed®. This material, however, may not be applied in a blood-rich environment as under such circumstances the material quickly loses its barrier function. Films formed from poly(ethyleneoxide) and polyethylene terephthalate have also been proposed as barrier materials to prevent surgical adhesions.

It would be advantageous to provide a device for preventing the binding of tissue to tissue or of tissue to bone wherein the device prevents such binding while being sufficiently pliable as well as providing for growth of tissue, such as fibrous tissue, into the device.

SUMMARY

Anti-adhesion devices in accordance with this disclosure have a first, film layer, and a second, gel layer. The film side inhibits the formation of post-operative adhesions and scarring, and the gel side acts as a tissue scaffold and promotes wound healing, cellular infiltration, angiogenesis, etc. The first layer, acting as a barrier layer, has a water content of less than about 40%; in some embodiments less than about 30%. The second layer, acting as a tissue growth promoter, has a water content of greater than about 40%; and in some embodiments between about 40% and 90%.

DETAILED DESCRIPTION OF PREFERRED EMBODIMENTS

Figure 1:
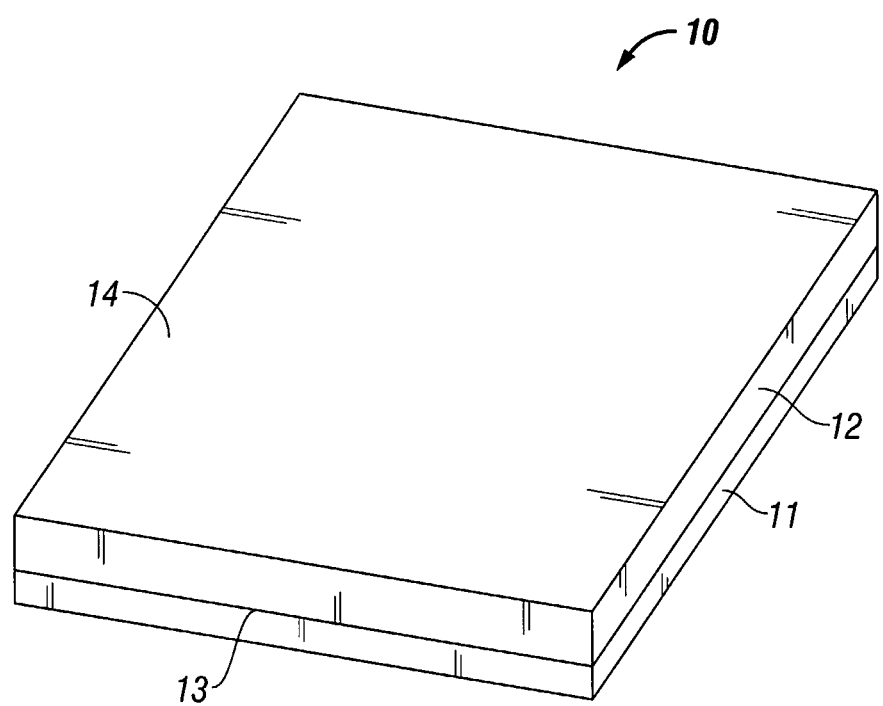
FIG. 1 is a schematic perspective view of an anti-adhesion device in accordance with is disclosure.

As seen in FIG. 1, an anti-adhesion device (generally denoted by the numeral 10) in accordance with this disclosure have a first, relatively smooth thin film layer 11, and a second gel layer 12. The film side inhibits the formation of post-operative adhesions and scarring, and the gel side acts as a tissue scaffold and promotes wound healing, cellular infiltration, angiogenesis, etc.

The layers of the present anti-adhesion devices are made from a hydrophilic biomaterial. Examples of suitable hydrophilic biomaterials include polymers formed from one or more of the following monomers: methacrylic acid, acrylic acid, n-vinyl pyrrolidone, potassium sulfopropylacrylate, potassium sulfopropylmethacrylate, acrylamide, dimethylacrylamide, 2-methacryloyloxyethyl phosphorylcholine, hydroxyethylmethacrylate or similar biocompatible water-soluble vinyl monomers. In a particularly useful embodiment, at least one of the layers is formed from a solution containing hydroxyethylmethacrylate.

Figure 2:
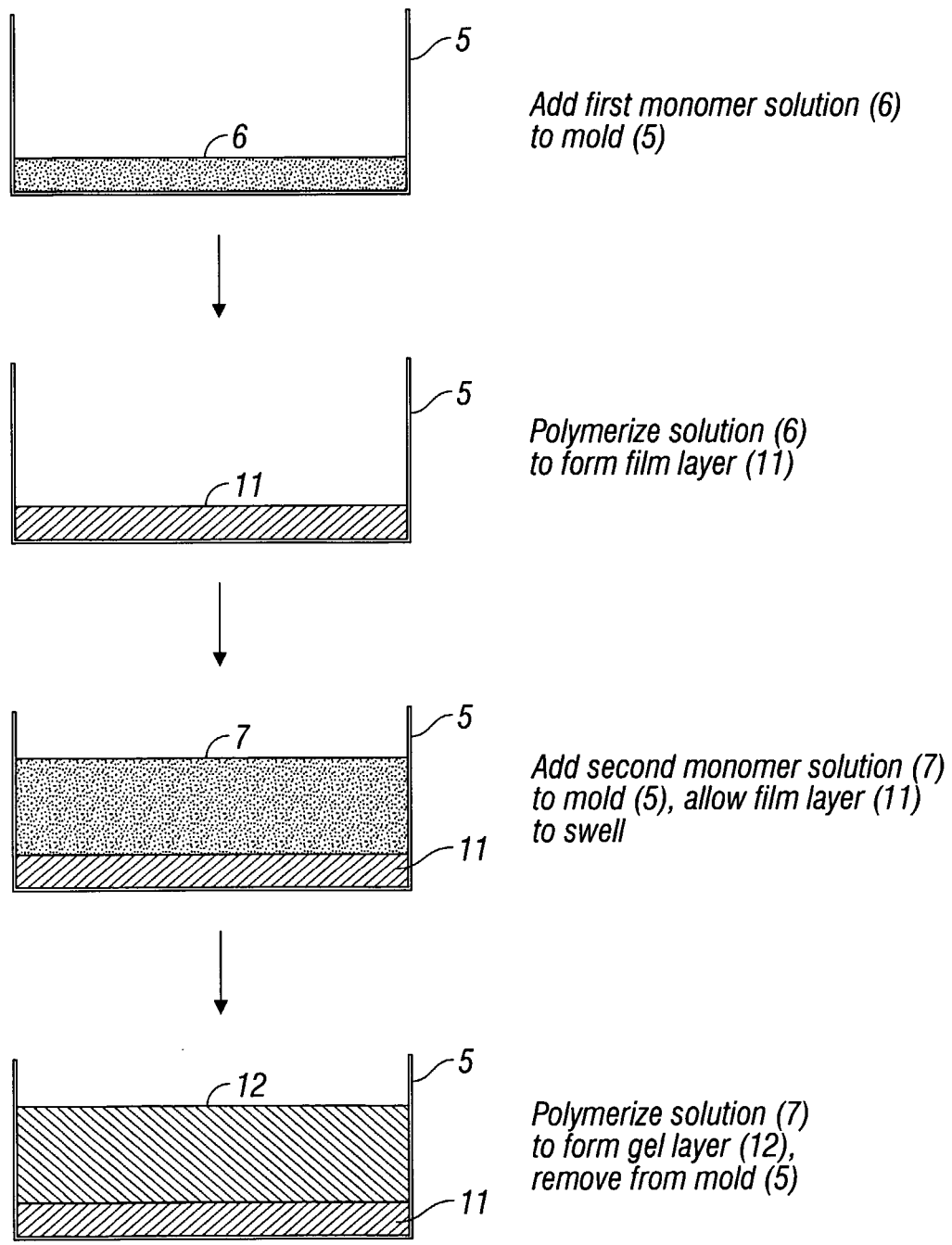
FIG. 2 is a schematic flow sheet showing the steps of one exemplary process for making an anti-adhesion device in accordance with is disclosure.

The present devices are prepared using techniques within the purview of those skilled in the art. FIG. 2 schematically shows one exemplary preparation process. As seen therein, the first, film side of the device can be formed by filling a mold 5 with a composition 6 containing the monomer(s) and, if desired or necessary, initiator, crosslinker, plasticizer and/or biological agent, and polymerizing the composition within the mold to form the film layer 11. The choice of particular initiators, crosslinkers, etc. will be determined by the specific choice of monomer(s).

The equilibrium water content (EWC), swelling, and mechanical properties of the film layer can be controlled by crosslink density (radiation conditions or crosslinker concentration). The thickness of the film side can be controlled by the volume of the monomer composition polymerized in the mold. Suitable thickness for the film side can be is in the range of about 0.1 to about 5 mm.

The second, gel side can be prepared in situ upon the first, film side by exposing the previously prepared layer 11 to an aqueous solution 8 containing one or more of the above-mentioned monomers suitable for making hydrophilic polymers. This will cause the original film to swell. The swollen film, while resting in the second biodegradable monomer or comonomer solution, can be incubated to further enhance film swelling prior to polymerization. The second monomer solution 7 is then polymerized in the presence of the swollen film 11 using low dose gamma radiation or conventional chemical initiated free radical polymerization or any other polymerization method within the purview of those skilled in the art to from the gel layer 12. The resulting structure is a composite containing two-layers; namely, a first film layer 11 of relatively low water content and a second gel layer 12 having a relatively high water content.

The equilibrium water content (EWC), swelling, and mechanical properties of the gel side can be controlled by crosslink density (radiation conditions or DEOGMA concentration). The thickness of the second, gel layer polymerized on top of the first, film layer, is controlled by varying the volume of monomer solution. As the volume of the second monomer solution increases, the thickness of the gels layer increases as well. Typically, the thickness of the second, gel layer will be in the range of about 0.1 to about 5 mm.

In the resulting composite, the gel layer is intimately associated with the relatively smooth thin film at the interface 13 between the two layers (see FIG. 1). During polymerization, the gel may form an interpenetrating network (IPN) of gel monomer/comonomers within the attached thin film and/or covalent interactions, i.e. grafting of gel monomers to the thin film during in situ polymerization. In addition, the water content of the resulting composite increases as you move from the interface 13 towards the outer surface 14 of the second layer.

The size, structure, and morphology of the gel can be controlled through monomer selection and concentration, reaction conditions (i.e. gamma dose and dose rate), solvents (water, buffered saline, media, etc.), agents incorporated (proteins, drugs, AM agents, etc.), and other parameters. The composites can also be lyophilized to produce a sponge-like morphology, on the second layer side, to assist in cell or tissue infiltration and wound healing, while retaining a smooth laminar surface on the film side.

In embodiments where the relatively smooth thin film side of the present anti-adhsion devices is made of poly-(hydroxyethyl methaerylate) (PHEMA), such films can be synthesized using $^{60}$Co gamma radiation, UV radiation, or conventional chemical initiated (AIBN, BPO, redox, etc.) free radical polymerization. In a typical preparation method, a composition containing HEMA monomer, AlBN as an initiator and diethyleneglycol dimethacrylate (DEGDMA) as a crosslinker is poured into a glass mold and polymerized at approximately 65° C. for 1.5 hours. Resulting films are washed repeatedly with water and dried in vacuo. In another preparation method, PHEMA the first side of the device can be prepared using radiation polymerization (600 mC source, 295-1180 rad/min, 0.05-1 Mrad) without the need of chemical initiator or crosslinker, and using the same washing/drying regiment.

The present anti-adhesion devices can be any shape, and will normally be in the form of a sheet. The devices can be made to size or prepared as a large sheet from which desired shapes are cut or punched. The present anti-adhesion devices can advantageously be provided as six inch square sheets which can be cut to any desired size or shape by the surgeon prior to application to tissue.

The present anti-adhesion devices can also be surface modified following film formation. For example, a PHEMA anti-adhesion device can be surface modified with polymeric phospholipids for improved hemocompatibility and tissue interaction using gamma radiation grafting.

In another embodiment, the surface of the anti-adhesion devices can be patterned or templated in the nano-meso-micro scale to accommodate preferential tissue interaction at the tissue/buttress interface. Such architecture or patterns can prevent or minimize post-operative tissue adhesions and superfluous collagen deposition, but afford desired mechanical and biophysical support for wound healing.

The composition from which each side of the anti-adhesion device is made may also contain one or more medically and/or surgically useful substances such as drugs, enzymes, growth factors, peptides, proteins, dyes, diagnostic agents or hemostasis agents or any other pharmaceutical used in the prevention of stenosis. Non-limiting examples of suitable medically and/or surgically useful substances include: anti-microbials, antibiotics, anti-fungals, anti-virals, monoclonal antibodies, polyclonal antibodies, antimicrobial proteins/peptides (whole and fragments), enzymes, gene therapy, viral particles, chemotherapeutics, anti-inflammatories, NSAIDS, steroids, telomerase inhibitors, growth factors (TGF family, interleukin superfamily, fibroblast derived GFs, macrophage derived GFs, etc.), extracellular matrix molecules (laminin, thrombospondin, collagen, fibronectin, synthetic ECM, etc.), cell adhesion molecules, polysaccharides (hyaluronic acid, carboxymethyl cellulose, alginate, sulfonated dextran, heparin sulfate, chitosan, etc.) and others. These agents can be incorporated in situ into the composition used the make each side of the anti-adhesion device or post loaded onto either or each polymerized side of the anti-adhesion device using techniques within the purview of those skilled in the art. For example, the medically and/or surgically useful substances can be freely mixed or loaded, electronically or ionically bound, covalently immobilized, chelated, or encapsulated in particles, micelles, aggregates, or any nano-meso-micro solids of varied dimension, shape morphology and dispersion/suspension ability.

It should be understood that the composition of the first and second layers can be the same or different, depending on the composition of the monomer solutions employed in making each layer and the presence of any medically and/or surgically useful substances or optional ingredients. Useful optional ingredients include, but are not limited too, plasticizers, emulsifiers, solvents, foaming agents, blowing agents, surfactants, radio-opaque markers, colors, dyes, fragrances, etc. These optional ingredients, when present, may be present in an amount of up to about 5 wt. % of the first layer and/or the second layer.

In another embodiment, the second layer may be coated with an adhesive such as, but not limited to, cellulose (such as carboxymethyl cellulose, or CMC, and hydroxypropyl methyl cellulose, or PIPMC); mucoadhesives, such as, but not limited to, mucin, mucopolysaccharides, polycarbophil, tragacanth, sodium alginate, gelatin, pectin, acacia, and providone; acrylates (such as polyacrylic acid and methyl methacrylate); polyoxyethylene glycol having a molecular weight of from about 100,000 to about 4,000,000; mixtures of zinc oxide and eugenol; a fibrin-glue layer; a chitosan layer; and glucosamine. Such a coating improves initial adhesion of the second layer of the device to tissue, such as the peritoneum.

It is also contemplated that a fibrous reinforcing element (not shown), such as a surgical grade mesh, can be incorporated into the anti-adhesion devices in accordance with the present disclosure. Suitable fibrous reinforcing elements can be made from a biocompatible non-absorbable (i.e., permanent) material, such as, for example "TEFLON" which is a registered trademark owned by DuPont de Nemours & Co., or a biocompatible absorbable material. The biocompatible materials can be woven, knit or non-woven. Bio-absorbable materials include those fabricated from homopolymers, copolymers or blends obtained from one or more monomers selected from the group consisting of glycolide, glycolic acid, lactide, lactic acid, p-dioxanone, $\epsilon$-caprolactone and trimethylene carbonate. Non-absorbable materials include those that are fabricated from such polymers as polyethylene, polypropylene, nylon, polyethylene terephthalate, polytetrafluoroethylene, polyvinylidene fluoride, and the like. Further non-absorbable materials include and are not limited to stainless steel, titanium and the like. To incorporate a fibrous reinforcing element into the present anti-adhesion devices, the reinforcing element can be added to the mold prior to addition of the monomer solution used to form the film layer. Alternatively, the reinforcing element can be placed on top of the film layer after it is formed, with the subsequent addition of the solution used to form the second, gel layer. Polymerization of the second solution will result in incorporation of the reinforcing element at or near the interface of the two layers.

The devices of the present disclosure may be employed as barriers between tissues or barriers between tissue and bone to prevent binding of tissue to tissue or of tissue to bone. Examples of uses of the devices of the present disclosure include, but are not limited to, barriers between the internal female reproductive organs (e.g., uterus, Fallopian tubes, ovaries); barriers between the internal female reproductive organs and the peritoneum; barriers for used during laparoscopy; barriers between periodontal tissue; barriers between cartilages or between cartilage and bone; barriers between digestive organs; spinal barriers; barriers between digestive organs and peritoneum; barriers between the epicardium and surrounding structures such as the pericardium, mediastinal fat, pleura, and sternum; barriers between tendons and tendon sheaths, such as those in the wrist and ankle; bone fracture wraps; barriers between muscle tissue and bone; barriers between the esophagus and mediasternum; barriers between the gall bladder or pancreas and the peritoneum; and barriers for scrotal surgery, i.e., hernias.

The devices of the present disclosure may also be used for guided tissue regeneration. For example, the devices may be used to cover internal perforations, such as, for example, perforations in blood vessels, internal organs, the nasal septum, and the eardrum membrane, and may be used to reconstruct the abdominal wall, or to reinforce areas prone to, or showing scar formation, such as, for example, inguinal hernias. The device therefore acts as a patch for covering the perforation until complete healing, followed by monomer absorption, is achieved. It is also contemplated that the devices may be employed as a cover for burns, whereby the device acts as a patch until the burn is healed.

The devices of the present disclosure may be employed as a scaffolding to treat ulcers. The second, growth promoting layer stimulates the proliferation of fibrous tissue, as a consequence of which, for example, in the case of ulcers, the wound bed becomes more optimal for the regeneration of skin.

The devices of the present disclosure may also be employed in redirect healing, whereby the devices are employed to protect nerves and organ coverings, and mucosa during the healing process, whereby the formation of fibrous tissue over such nerves, organs, and mucosa is prevented.

The devices may also be employed to prevent the formation of internal blood clots after surgery or traumatic injury.

The devices may also be employed in covering denuded epithelial surfaces or weakened areas such as damaged middle ear mucosa or other mucosal surfaces, thinned vascular walls, or surgically denuded areas, such as, for example, surgically denuded areas of the pelvis.

The devices may also be employed as anti-fibroblastic growth barriers, or as nerve coaptation wraps for connecting or repairing severed nerve ends or for repairing inflamed nerves.

Since the resulting composites of the present disclosure are easily moldable, malleable and bendable, these devices may also be used with a wide variety of different medical devices, such as sutures, anchors, implants, scaffolds, staples, etc.

The present anti-adhesion devices can be sterilized and package using techniques within the purview of those skilled in the art. The method of sterilization should be chosen to preserve the efficacy of any medically and/or surgically useful substances contained in the device. The device may be packaged in a pre-swollen or "wet" state which may lessen the devices shelf-life. Also, the device may be packaged in a "dry" or non-swollen state wherein the device could be pre-swollen prior to use or could swell in situ upon contact with natural bodily fluids. Such a packaging may lengthen the shelf-life of the device.

While the above disclosure has related generally to specific embodiments of anti-adhesion devices and their use, it is to be understood, however, that the scope of the present disclosure is not to be limited to the specific embodiments described above. For example, rather than sheets, the present layered devices can be formed into tubular structures. As another example, the present devices are not limited to two layers, but rather more than two layers can be prepared, if desired using the presently described techniques. Therefore, the above description should not be construed as limiting, but merely as exemplifications of preferred embodiments. Those skilled in the art will envision other modifications within the scope and spirit of the present disclosure.

What is claimed is:

1. An anti-adhesion device comprising: a composite of a first layer and a second layer, wherein the first layer comprises a film comprising a hydrophilic polymer and a water content less than 40% and the second layer comprises a gel comprising a hydrophilic polymer and a water content greater than 40%, wherein the film prevents adhesions and the gel promotes tissue growth.

2. The anti-adhesion device of claim 1 wherein the hydrophilic polymer of the first layer is formed from at least one monomer is selected from the group consisting of poly-(hydroxyethyl methacrylate), methacrylic acid, acrylic acid, n-vinyl pyrrolidone, potassium sulfopropylacrylate, potassium sulfopropylmethacrylate, hydroxethyl methacrylate, acrylamide, dimethylacrylamide, 2-methacryloyloxyethyl phosphorylcholine and combinations thereof.

3. The anti-adhesion device of claim 1 wherein the hydrophilic polymer of the first layer is formed from poly (hydroxyethyl methacrylate).

4. The anti-adhesion device of claim 1 wherein the hydrophilic polymer of the second layer is formed from at least one monomer selected from the group consisting of poly (hydroxyethyl methacrylate), methacrylic acid, acrylic acid, n-vinyl pyrrolidone, potassium sulfopropylacrylate, potassium sulfopropylmethacrylate, hydroxyethyl methacrylate, acrylamide, dimethylacrylamide, 2-methacryloyloxyethyl phosphorylcholine and combinations thereof.

5. The anti-adhesion device of claim 1 wherein the hydrophilic polymer of the second layer is formed from poly (hydroxyethyl methacrylate).

6. The anti-adhesion device of claim 1 further comprising a biological agent selected from the group consisting of antimicrobials, antibiotics, antimitotics, anti-fungal, anti-viral, mono and polyclonal antibodies, antimicrobial proteins, whole antimicrobial peptides, fragmented antimicrobial peptides, enzymes, genetic therapy, viral particles, chemotherapeutics, anti-inflammatories, NSAIDS, steroids, telomerase inhibitors, growth factors, ECM molecules, cell adhesion molecules, polysaccharides, dyes, and combinations thereof.

7. A process for forming an anti-adhesion device comprising: polymerizing a first biodegradable monomer to form a first layer, swelling the first layer in a second biodegradable monomer, and polymerizing the swelling first layer in the second biodegradable monomer to form a composite, wherein the first layer comprises a film comprising a hydrophilic polymer and a water content less than 40% and the second layer comprises a gel comprising a hydrophilic polymer and a water content greater than 40%, wherein the film prevents adhesions and the gel promotes tissue growth.

8. The process of claim 7 further comprising the step of incubating the swelling first layer in the second biodegradable monomer prior to polymerization.

9. A process for preventing the binding of tissue to tissue or of tissue to bone comprising: placing between two tissues or between tissue and bone a device comprising a composite of a first and second layer, wherein the first layer comprises a film comprising a hydrophilic polymer and a water content less than 40%, and the second layer comprises a gel comprising a hydrophilic polymer and a water content great than 40%, wherein the film prevents adhesions and the gel promotes tissue growth.

10. The process of claim 9 wherein the step of placing between two tissues or between tissue and bone a device comprising a composite of a first and second layer, wherein the hydrophilic polymer of the first layer comprises a first biodegradable monomer selected from the group consisting of poly (hydroxyethyl methacrylate), methacrylic acid, acrylic acid, n-vinyl pyrrolidone, potassium sulfopropylacrylate, potassium sulfopropylmethacrylate, hydroxyethyl methacrylate, acrylamide, dimethylacrylamide, 2-methacryloyloxyethyl phosphorylcholine and combinations thereof.

11. The process of claim 9 wherein the step of placing between two tissues or between tissue and bone a device comprising a composite of a first and second layer, wherein the hydrophilic polymer of the second layer comprises a second biodegradable monomer selected from the group consisting of poly (hydroxyethyl methacrylate), methacrylic acid, acrylic acid, n-vinyl pyrrolidone, potassium sulfopropylacrylate, potassium sulfopropylmethacrylate, hydroxyethyl methacrylate, acrylamide, dimethylacrylamide, 2-methacryloyloxyethyl phosphorylcholine and combinations thereof.

12. The process of claim 9 wherein the step of placing between two tissues or between tissue and bone a device comprising a composite of a first and second layer, wherein the first layer comprises poly (hydroxyethyl methacrylate).

13. The process of claim 9 wherein the step of placing between two tissues or between tissue and bone a device comprising a composite of a first and second layer, wherein the second layer comprises poly (hydroxyethyl methacrylate).

* * * * *